(12) United States Patent
Higuchi et al.

(10) Patent No.: US 8,486,450 B2
(45) Date of Patent: Jul. 16, 2013

(54) METHOD OF PRODUCING SOLID PREPARATION DISINTEGRATING IN THE ORAL CAVITY

(75) Inventors: Shigehiro Higuchi, Osaka (JP); Hiroshi Fukada, Osaka (JP); Toshihide Saito, Osaka (JP); Tetsuro Tabata, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 740 days.

(21) Appl. No.: 12/087,107

(22) PCT Filed: Dec. 27, 2006

(86) PCT No.: PCT/JP2006/326022
§ 371 (c)(1),
(2), (4) Date: Jun. 26, 2008

(87) PCT Pub. No.: WO2007/074856
PCT Pub. Date: Jul. 5, 2007

(65) Prior Publication Data
US 2009/0148524 A1 Jun. 11, 2009

(30) Foreign Application Priority Data
Dec. 28, 2005 (JP) .................................. 2005-379809

(51) Int. Cl.
*A61K 9/20* (2006.01)
*A61K 9/16* (2006.01)

(52) U.S. Cl.
USPC .......................................... 424/465; 424/490

(58) Field of Classification Search
None
See application file for complete search history.

(56) References Cited

U.S. PATENT DOCUMENTS
6,328,994 B1 12/2001 Shimizu et al.
2002/0142034 A1 10/2002 Shimizu et al.

FOREIGN PATENT DOCUMENTS

| | | |
|---|---|---|
| EP | 1 203 580 | 5/2002 |
| EP | 1203580 A1 * | 5/2002 |
| EP | 1 405 621 | 4/2004 |
| EP | 1 488 811 | 12/2004 |
| JP | 2000-281564 | 10/2000 |
| WO | 97/38960 | 10/1997 |
| WO | WO 9738960 A1 * | 10/1997 |
| WO | 99/59544 | 11/1999 |
| WO | 00/06126 | 2/2000 |
| WO | WO 0006126 A1 * | 2/2000 |
| WO | 2007/043538 | 4/2007 |

OTHER PUBLICATIONS

English translation of Aichi-ken Byoin Yakuzaishikai Zasshi (APJHP) (ISSN 1340-8801), J. Kikuta et al., "How Takepron OD Tablets Were Developed", APJHP, vol. 32, No. 2, pp. 33-36, 2004.
T. Shimizu et al., "Formulation Study for Lansoprazole Fast-Disintegrating Tablet. III. Design of Rapidly Disintegrating Tablets", Chem. Pharm. Bull., vol. 51, No. 10, pp. 1121-1127, 2003.
J. Kikuta et al., "Takepron OD-jo ga Tanjo Suru Made", Aichi-Ken Byoin Yakuzaishikai Zasshi (APJHP) (ISSN 1340-8801), vol. 32, No. 2, pp. 33-36, 2004 (in Japanese).
T. Yoshinari et al., "The Improved Compaction Properties of Mannitol after a Moisture-Induced Polymorphic Transition", International Journal of Pharmaceutics, vol. 258, pp. 121-131, 2003.
Parteck Delta M—Merck Pamphlet (Publication Date: Apr. 7, 2004).
Supplementary European Search Report issued Nov. 27, 2009 in European Application No. EP 06 84 3404.
A. Burger et al., "Energy/Temperature Diagram and Compression Behavior of the Polymorphs of D-Mannitol", Journal of Pharmaceutical Sciences, American Pharmaceutical Association, vol. 89, No. 4, pp. 457-468, Apr. 2000.

* cited by examiner

*Primary Examiner* — Susan Tran
(74) *Attorney, Agent, or Firm* — Wenderoth, Lind & Ponack, L.L.P.

(57) ABSTRACT

It is intended to provide a method of producing a solid preparation disintegrating in the oral cavity characterized by comprising mixing fine subtilaes containing a medicinal ingredient with an additive containing δ-mannitol and tableting the mixture; and a solid preparation disintegrating in the oral cavity produced thereby. This solid preparation disintegrating in the oral cavity has such a strength (hardness) as suffering from no defect even under stresses in transporting, packaging with the use of an automated packaging machine, taking out from a PTP and soon.

12 Claims, No Drawings

METHOD OF PRODUCING SOLID PREPARATION DISINTEGRATING IN THE ORAL CAVITY

This application is a U.S. national stage of International Application No. PCT/JP2006/326022 filed Dec. 27, 2006.

TECHNICAL FIELD

The present invention relates to a method of producing an orally disintegrating solid preparation of which strength (hardness) is improved so that the occurrence of damage in said preparation can be suppressed when the preparation is subjected to a stress in conveying, packaging with the use of an automatic dispenser, taking out from a PTP and so on.

BACKGROUND ART

Recently, solid preparations disintegrating in the oral cavity which can be easily ingested by elderly people and children without water have been frequently developed because they are very convenient. The following known documents disclose such preparations.

Japanese Patent Application Laid-Open (JP-A) No. 2000-281564 (Patent Document 1) discloses an orally disintegrating tablet containing microgranules having an average particle diameter of 400 μm or less and an additive, wherein said granules are prepared by coating a composition containing 10% by weight or more of an acid-labile physiologically active substance with an enteric coating layer.

JP-A 2000-103731 (Patent Document 2) discloses a rapidly disintegrating solid preparation containing 1) an active pharmaceutical ingredient, 2) a sugar and 3) a low-substituted hydroxypropyl cellulose having 5% by weight or more to less than 7% by weight of a hydroxypropoxyl group.

JP-A 2003-081814 (Patent Document 3) discloses a method of producing a tablet which comprises tableting a coated particle containing a physiologically active substance at a temperature exceeding room temperature.

On the other hand, JP-A 10-036291 (Patent Document 4) discloses D-mannitol which can be used as an excipient excellent in moldability, and a method of producing the same.

The aforementioned known documents do not describe a method of producing an orally disintegrating solid preparation which comprises mixing microgranules containing an active pharmaceutical ingredient with an additive containing δ-mannitol and then tableting the mixture.

Patent Document 1: JP-A 2000-281564
Patent Document 2: JP-A 2000-103731
Patent Document 3: JP-A 2003-081814
Patent Document 4: JP-A 10-036291

DISCLOSURE OF THE INVENTION

Problems to be Solved by the Invention

In general industrial production of a solid preparation such as a tablet, the hardness of a tablet is increased to some extent by using a high pressure for tableting, thereby the possibility of breaking or chipping in conveying or the like can be reduced to some extent. However, an increase of a tableting pressure is mechanically restricted, and the hardness of a tablet obtained by tableting has a limitation. On the other hand, in the case of a tablet rapidly disintegrating in the oral cavity, it is necessary to adjust the hardness of the tablet to a suitable hardness so that the tablet can disintegrate rapidly in the oral cavity, and the tablet should not be excessively hard. For this reason, it is necessary to take measures such as attachment of a buffer material to the inner surface of a conveying path and reduction of a conveying speed so that a tablet is not damaged by a stress when the tablet is contacted with other substances during conveying. Thus, maintenance of a whole tableting machine is troublesome and expensive. Therefore, there is a problem that improvement in productivity is not easy. In addition, there is a possibility that a tablet is damaged by a pushing pressure, for example, in packaging with the use of an automatic dispenser or taking out from a PTP, and there is a problem that it is not easy to suppress such damage occurrence.

A technical objective of the present invention is to solve the aforementioned problems, and provide a method of producing a rapidly disintegrating solid preparation having a suitable strength (hardness) by using a tableting pressure within a usually industrially adopted range, wherein the occurrence of damage in said preparation can be suppressed when the preparation is subjected to a stress in conveying, packaging with the use of an automatic dispenser or taking out from a PTP and so on, and said preparation can rapidly disintegrate in the oral cavity in the presence of saliva or a small amount of water in the oral cavity.

Means for Solving Problem

Inventors of the present invention intensively studied in order to solve the aforementioned problems, and as a result, found that an orally disintegrating solid preparation having a desired suitable strength (hardness) can be produced by using δ-mannitol as an excipient. Then the present invention was completed.

That is, the present invention relates to:
(1) a method of producing an orally disintegrating solid preparation, which comprises mixing microgranules containing an active pharmaceutical ingredient with an additive containing δ-mannitol, and then tableting the mixture;
(2) the method according to the above (1), which comprises a step of contacting δ-mannitol with an aqueous solvent;
(3) the method according to the above (1), wherein the additive containing δ-mannitol further contains (i) crystalline cellulose and/or (ii) low-substituted hydroxypropyl cellulose;
(4) the method according to the above (1), wherein the additive containing δ-mannitol is granulated by a fluidized bed granulation method;
(5) the method according to the above (4), wherein the fluidized bed granulation comprises a spraying step of a δ-mannitol solution and a drying step;
(6) the method according to the above (5), wherein the solution is an aqueous solution;
(7) the method according to the above (4), wherein dried granules of the additive are produced by a fluidized bed granulation method and the resulting dried granules are subjected to size adjustment;
(8) the method according to the above (1), wherein the active pharmaceutical ingredient is an acid-labile physiologically active substance;
(9) the method according to the above (1), wherein the active pharmaceutical ingredient is a proton pump inhibitor (PPI);
(10) the method according to the above (8), wherein the acid-labile physiologically active substance is a benzimidazole compound or a salt thereof;
(11) the method according to the above (10), wherein the benzimidazole compound is lansoprazole or a salt thereof, or an optically active form thereof;

(12) the method according to the above (1), wherein the average particle diameter of the microgranules is 400 μm or less;
(13) the method according to the above (12), wherein a basic inorganic salt is present in the microgranules;
(14) the method according to the above (12), wherein the microgranules are coated with an enteric coating layer;
(15) an orally disintegrating solid preparation obtained by using the method according to the above (1);
(16) the orally disintegrating solid preparation according to the above (15), which has a strength (a value measured with a tablet hardness tester) of about 10 N to about 150 N; and
(17) the orally disintegrating solid preparation according to the above (15), which has an oral disintegration time of within 90 seconds.

Effect of the Invention

According to the production method of the present invention, an orally disintegrating solid preparation having a suitable strength (hardness) can be produced, and therefore the occurrence of damage in the preparation can be suppressed when the preparation is subjected to a stress in conveying, packaging with the use of an automatic dispenser, taking out from a PTP and so on.

An orally disintegrating solid preparation obtained by the production method of the present invention has excellent disintegrating property or excellent solubility, and therefore it can be used in treating and preventing various diseases as a preparation which can be easily ingested by elderly people and children without water.

In addition, an orally disintegrating solid preparation obtained by the production method of the present invention has a suitable strength, and therefore it also has excellent long-term storage stability.

Further, an orally disintegrating solid preparation obtained by the production method of the present invention does not have a powdery mouthfeel, and therefore it has a pleasant mouth feel.

Mannitol, particularly D-mannitol is crystalline powder having crystal polymorphism which is classified into α-, β- and δ-forms based on X-ray diffraction patterns. As used herein, α-, β- and δ-D-mannitol crystals are defined according to the classification of crystal polymorphism of D-mannitol on the basis of X-ray diffraction patterns reported by Walter-Levy, L. [Acad. Sci. Paris t. 276 Series C, 1779, (1968)].

In the production method of the present invention, δ-D-mannitol (hereinafter, abbreviated as δ-mannitol in some cases) is used. Only δ-crystals may be used or a mixture of δ-crystals and other crystal forms such as β-crystals may be used. In the case of using a mixture, mannitol comprising about 70% or more, preferably about 80% or more of δ-mannitol is desirably used. In addition, a D-mannitol crystal aggregate comprising δ-mannitol having a specific surface area of about 0.1 m$^2$/g or more, preferably about 0.3 m$^2$/g or more, usually about 0.3 to about 0.6 m$^2$/g is preferred. Herein, a specific surface area is a numerical value calculated by a BET method which is generally widely used. From the viewpoint of convenience in utilization as an additive or an excipient for a medicine or a food, it is preferable that mannitol is an aggregate of particulate crystals, inter alia, having an average particle diameter of about 0.05 to about 5.0 mm, further preferably about 0.08 to about 2.0 mm. However, the shape of the crystal is not particularly limited and may be net-like or thin plate-like.

Examples of commercially available δ-mannitol include ParTeck Delta M of Merck and D-mannitol (low endotoxin).

In 100 parts by weight of a whole pharmaceutical preparation, δ-mannitol is used in an amount of usually about 15 to 80 parts by weight, preferably about 20 to 75 parts by weight.

An active pharmaceutical ingredient used in the present invention may be in any form of a solid, a powder, a crystal, an oil, a solution and the like. Examples of the active pharmaceutical ingredient include a tonic, an antipyretic analgesic antiphlogistic, a psychotropic agent, an antianxiety agent, an antidepressant, a hypnotic sedative, an anticonvulsant, a central nervous system drug, a brain metabolism improving agent, a brain circulation improving agent, an antiepileptic agent, a sympathomimetic stimulant, a gastrointestinal agent, an antacid, an antiulcer agent, an antitussive expectorant, an antiemetic, a respiratory accelerator, a bronchodilator, an antiallergy agent, a dental agent for oral use, an antihistamine, a inotropic agent, an agent for arrhythmia, a diuretic, a blood pressure lowering agent, a vasoconstrictor, a coronary vasodilator, a peripheral vasodilator, an agent for hyperlipemia, a cholagogue, an antibiotic, a chemotherapeutic agent, an agent for diabetes, an agent for osteoporosis, an antirheumatic, a skeletal muscle relaxant, an antispasmodic, a hormone agent, an alkaloidal narcotic, a sulfa drug, a gout remedy, a blood coagulation inhibitor, an anti-malignant tumor agent, an Alzheimer's disease remedy and the like, and one or more selected from the aforementioned ingredients are used.

Examples of the tonic include vitamins such as vitamin A, vitamin D, vitamin E (d-α-tocopherol acetate, etc.), vitamin $B_1$ (dibenzoylthiamine, fursultiamine hydrochloride, etc.), vitamin $B_2$ (riboflavin butyrate, etc.), vitamin $B_6$ (pyridoxine hydrochloride, etc.), vitamin C (ascorbic acid, sodium L-ascorbate, etc.), and vitamin $B_{12}$ (hydroxocobalamin acetate, cyanocobalamin, etc.), minerals such as calcium, magnesium and iron, proteins, amino acids, oligosaccharides, galenicals, and the like.

Examples of the antipyretic analgesic antiphlogistic include aspirin, acetaminophen, ethenzamide, ibuprofen, diphenhydramine hydrochloride, dl-chlorphenylamine maleate, dihydrocodeine phosphate, noscapine, methylephedrine hydrochloride, phenylpropanolamine hydrochloride, caffeine, caffeine anhydride, serrapeptase, lysozyme chloride, tolfenamic acid, mefenamic acid, diclofenac sodium, flufenamic acid, salicylamide, aminopyrine, ketoprofen, indometacin, bucolome, pentazocine, and the like.

Examples of the psychotropic agent include chlorpromazine, reserpine, and the like.

Examples of the antianxiety agent include alprazolam, chlordiazepoxide, diazepam, and the like.

Examples of the antidepressant include imipramine, maprotiline hydrochloride, amphetamine, and the like.

Examples of the hypnotic sedative include estazolam, nitrazepam, diazepam, perlapine, phenobarbital sodium, and the like.

Examples of the anticonvulsant include scopolamine hydrobromide, diphenhydramine hydrochloride, papaverine hydrochloride, and the like.

Examples of the central nervous system drug include citicoline, and the like.

Examples of the brain metabolism improving agent include meclofenoxate hydrochloride, and the like.

Examples of the brain circulation improving agent include vinpocetine, and the like.

Examples of the antiepileptic include phenyloin, carbamazepine, and the like.

Examples of the sympathomimetic stimulant include isoproterenol hydrochloride, and the like.

Examples of the gastrointestinal agent include stomachic digestive agents such as diastase, sugar-containing pepsine, scopolia extract, cellulase AP3, lipase AP, and cinnamic oil, and agents for controlling intestinal function such as berberine chloride, resistant lactobacillus, bifidobacteria, and the like.

Examples of the antacid include magnesium carbonate, sodium hydrogen carbonate, magnesium aluminate metasilicate, synthetic hydrotalcite, precipitated calcium carbonate, magnesium oxide, and the like.

Examples of the antiulcer agent include lansoprazole, omeprazole, rabeprazole, pantoprazole, ilaprazole, tenatoprazole, famotidine, cimetidine, ranitidine hydrochloride, and the like.

Examples of the antitussive expectorant include cloperastine hydrochloride, dextromethorphan hydrobromide, theophylline, potassium guaiacolsulfonate, guaifenesin, codeine phosphate, and the like.

Examples of the antiemetic include difenidol hydrochloride, metoclopramide, and the like.

Examples of the respiratory accelerator include levallorphan tartrate, and the like.

Examples of the bronchodilator include theophylline, salbutamol sulfate, and the like.

Examples of the antiallergy agent include amlexanox, seratrodust, and the like.

Examples of the dental agent for oral use include oxytetracycline, triamcinolone acetonide, chlorhexidine hydrochloride, lidocaine, and the like.

Examples of the antihistamine include diphenhydramine hydrochloride, promethazine, isothipendyl hydrochloride, dl-chlorphenylamine maleate, and the like.

Examples of the inotropic agent include caffeine, digoxin, and the like.

Examples of the agent for arrhythmia include procainamide hydrochloride, propranolol hydrochloride, pindolol, and the like.

Examples of the diuretic include isosorbide, furosemide, a thiazide agent such as HCTZ, and the like.

Examples of the blood pressure lowering agent include delapril hydrochloride, captopril, hexamethonium bromide, hydralazine hydrochloride, labetalol hydrochloride, manidipine hydrochloride, candesartan cilexetil, methyldopa, losartan, valsartan, eposartan, irbesartan, tasosartan, telmisartan, and the like.

Examples of the vasoconstrictor include phenylephrine hydrochloride, and the like.

Examples of the coronary vasodilator include carbochromen hydrochloride, molsidomine, verapamil hydrochloride, and the like.

Examples of the peripheral vasodilator include cinnarizine, and the like.

Examples of the agent for hyperlipemia include cerivastatin sodium, simvastatin, pravastatin sodium, and the like.

Examples of the cholagogue include dehydrocholic acid, trepibutone, and the like.

Examples of the antibiotic include cephem antibiotics such as cephalexin, cefaclor, amoxicillin, pivmecillinam hydrochloride, cefotiam hexetil hydrochloride, cefadroxil, cefixime, cefditoren pivoxil, cefteram pivoxil, cefpodoxime proxetil, cefotiam hydrochloride, cefozopran hydrochloride, cefmenoxime hydrochloride, and cefsulodin sodium, synthetic antibacterial agents such as ampicillin, ciclacillin, sulbenicillin sodium, nalidixic acid, and enoxacin, monobactam antibiotics such as carumonam sodium, penem antibiotics, carbapenem antibiotics, and the like.

Examples of the chemotherapeutic agent include sulfamethizole, sulfamethizole hydrochloride, thiazosulfone, and the like.

Examples of the agent for diabetes include tolbutamide, pioglitazone hydrochloride, glibenclamide, trog-litazone, rosiglitazone maleate, acarbose, miglitol, emiglitate (excluding voglibose), and the like.

Examples of the agent for osteoporosis include ipriflavone, and the like.

Examples of the skeletal muscle relaxant include methocarbamol, and the like.

Examples of the antispasmodic include meclizine hydrochloride, dimenhydrinate, and the like.

Examples of the antirheumatic include methotrexate, bucillamine, and the like.

Examples of the hormone agent include liothyronine sodium, dexamethasone sodium phosphate, predonisolone, oxendolone, leuprorelin acetate, and the like.

Examples of the alkaloidal narcotic include opium, morphine hydrochloride, ipecac, oxycodone hydrochloride, opium alkaloid hydrochloride, cocaine hydrochloride, and the like.

Examples of the sulfa drug include sulfamine, sulfisomidine, sulfamethizole, and the like.

Examples of the gout remedy include allopurinol, colchicine, and the like.

Examples of the blood coagulation inhibitor include dicoumarol, and the like.

Examples of the anti-malignant tumor agent include 5-fluorouracil, uracil, mitomycin, and the like.

Examples of the Alzheimer's disease remedy include idebenone, vinpocetine, and the like.

Among the aforementioned active pharmaceutical ingredients, an antiulcer agent is preferably used.

The active pharmaceutical ingredient is preferably an acid-labile physiologically active substance.

Examples of the "acid-labile physiologically active substance" include compounds (active pharmaceutical ingredients) which are labile in an acidic region and/or inactivated by an acid, and specific examples thereof include vitamin compounds (vitamin $B_{12}$, fursultiamine, folic acid, vitamin A, vitamin D, etc.), and known benzimidazole compounds having antiulcer activity represented by the Formula (I):

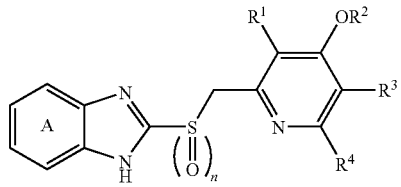

wherein the ring A may be substituted, $R^1$, $R^3$ and $R^4$ are the same or different and represent hydrogen, an alkyl group or an alkoxy group, $R^2$ represents a $C_{1-4}$ alkyl group optionally substituted with a substituent selected from halogen, a hydroxy group and a $C_{1-4}$ alkoxy group, and n represents 0 or 1; and a salt thereof.

When the ring A is substituted in the Formula (I), examples of a substituent include a halogen atom, an optionally substituted $C_{1-10}$ alkyl group, an optionally substituted $C_{3-7}$ cycloalkyl group, an optionally substituted $C_{2-16}$ alkenyl group, an optionally substituted $C_{1-110}$ alkoxy group, a cyano group, a carboxy group, a $C_{1-7}$ alkoxycarbonyl group, a $C_{1-4}$ alkoxycarbonyl-$C_{1-4}$ alkyl group, a carbamoyl group, a carbamoyl-$C_{1-4}$ alkyl group, a hydroxy group, a hydroxy-$C_{1-7}$ alkyl group, a $C_{1-6}$ acyl group, a carbamoyloxy group, a nitro group, a $C_{2-6}$ acyloxy group, a $C_{6-12}$ aryl group, a $C_{6-12}$ aryloxy group, a $C_{1-6}$ alkylthio group, a $C_{1-6}$ alkylsulfinyl group, a 1-pyrrolyl group and the like.

Examples of a substituent for the "optionally substituted $C_{1-10}$ alkyl group", the "optionally substituted $C_{3-7}$ cycloalkyl group" and the "optionally substituted $C_{2-16}$ alkenyl group" include (1) halogen, (2) nitro, (3) an amino group optionally having 1 to 2 substituents such as a $C_{1-4}$ alkyl group, a $C_{1-4}$ acyl group and the like, (4) an amidino group, (5) a guanidino group, (6) a carbamoyl group and the like. The number of these substituents is around 1 to 3.

Examples of a substituent for the "optionally substituted $C_{1-10}$ alkoxy group" include (1) halogen, (2) nitro, (3) an amino group optionally having 1 to 2 substituents such as a $C_{1-4}$ alkyl group, a $C_{1-4}$ acyl group and the like, (4) an amidino group, (5) a guanidino group and the like. The number of the substituents is around 1 to 3.

Examples of the "$C_{1-6}$ acyl group" include a formyl group, a $C_{2-6}$ alkanoyl group such as acetyl and propionyl, and the like. Examples of the "$C_{1-4}$ acyl group" include a formyl group, a $C_{2-4}$ alkanoyl group such as acetyl and propionyl, and the like.

Examples of the "$C_{2-6}$ acyloxy group" include a $C_{2-6}$ alkanoyloxy group such as acetyloxy, and the like.

Examples of the "$C_{6-12}$ aryl group" include phenyl, naphthyl, and the like.

Examples of the "$C_{6-12}$ aryloxy group" include phenoxy, naphthyloxy, and the like.

Examples of the alkyl group represented by $R^1$, $R^3$ or $R^4$ include a straight or branched $C_{1-10}$ alkyl group, and specific examples thereof include methyl, ethyl, n-propyl, isopropyl, n-butyl, isobutyl, sec-butyl, tert-butyl, n-pentyl, isopentyl, neopentyl, hexyl, heptyl, octyl, nonyl, decyl and the like. Among them, a straight or branched $C_{1-6}$ alkyl group is preferred. A straight or branched $C_{1-3}$ alkyl group is particularly preferred.

Examples of an alkoxy group represented by $R^1$, $R^3$ or $R^4$ include a $C_{1-10}$ alkoxy group, and specific examples thereof include methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, cyclobutoxy, cyclopentoxty, cyclohexyloxy, and the like. Among them, a $C_{1-6}$ alkoxy group is preferred. A $C_{1-3}$ alkoxy group is particularly preferred.

Examples of the "$C_{1-4}$ alkyl group" of the "$C_{1-4}$ alkyl group optionally substituted with a substituent selected from halogen, a hydroxy group and a $C_{1-4}$ alkoxy group" represented by $R^2$ include methyl, ethyl, n-propyl, isopropyl, n-butyl, isobutyl, sec-butyl, tert-butyl, and the like.

Examples of the "$C_{1-4}$ alkoxy group" of the "$C_{1-4}$ alkyl group optionally substituted with a $C_{1-4}$ alkoxy group" include methoxy, ethoxy, n-propoxy, isopropoxy, n-butoxy, isobutoxy, sec-butoxy, tert-butoxy, and the like.

In the $C_{1-4}$ alkyl group represented by $R^2$, the number of substituents is preferably 1 to 3.

Examples of a salt of the benzimidazole compound include a salt with a physiologically acceptable base such as a salt with an alkali metal such as sodium or potassium, a salt with an alkaline earth metal such as calcium or magnesium, and the like.

Examples of the "benzimidazole compound having antiulcer activity or a salt thereof" include compounds or salts thereof described in JP-A 52-62275, JP-A 54-141783, JP-A 57-53406, JP-A 58-135881, JP-A 58-192880, JP-A 59-181277, JP-A 61-50978, JP-A 62-116576, JP-A 62-277322, JP-A 62-258320, JP-A 62-258316, JP-A 64-6270, JP-A 64-79177, JP-A 5-59043, JP-A 62-111980, JP-A 5-117268, EP 166287A, and EP 519365A.

As the active pharmaceutical ingredient, a proton pump inhibitor such as lansoprazole, omeprazole, rabeprazole, pantoprazole, ilaprazole or tenatoprazole, or an optically active form thereof is preferred, and lansoprazole or a salt thereof or an optically active form thereof is particularly preferred.

Two or more kinds of the active pharmaceutical ingredients may be incorporated in a preparation.

The active pharmaceutical ingredient may be diluted with a diluent which is conventionally used in the medical or food field. The active pharmaceutical ingredient may be treated for the purpose of masking bitterness.

The active pharmaceutical ingredient is used in an amount of for example 0.01 to 70 parts by weight, preferably 0.02 to 50 parts by weight, further preferably 0.05 to 30 parts by weight, in 100 parts by weight of a solid preparation.

The orally disintegrating solid perpetration of the present invention is produced by using the δ-mannitol as an additive such as an excipient. In addition to the δ-mannitol and the active pharmaceutical ingredient, for example, water-soluble sugar alcohol, crystalline cellulose or low-substituted hydroxypropyl cellulose can be used as necessary. The orally disintegrating solid perpetration for oral administration can be produced by further adding and mixing a binder, an acidulant, an effervescent agent, an artificial sweetener, a flavor, a lubricant, a colorant, a stabilizing agent, an excipient, a disintegrant, and the like to the δ-mannitol and the active pharmaceutical ingredient and, if necessary, water-soluble sugar alcohol, crystalline cellulose or low-substituted hydroxypropyl cellulose, and then compression molding the mixture, according to a known method. Alternatively, a dispersion of the active pharmaceutical ingredient in water can be placed in a mold (e.g. PTP molded pocket), dried with a lyophilizer or a circulation dryer, and then heat-sealed to obtain a molded tablet.

The term "water-soluble sugar alcohol" means a sugar alcohol which requires less than 30 ml of water for dissolution within about 30 minutes when 1 g of the sugar alcohol is added to water and then strongly shaken at 20° C. for 30 seconds every 5 minutes.

Examples of the "water-soluble sugar alcohol" include sorbitol, maltitol, a hydrogenated starch hydrolysate, xylitol, reduced palatinose, erythritol, and the like. The water-soluble sugar alcohol may be a mixture of two or more kinds of them at an appropriate ratio.

Although the δ-mannitol is also an additive included in "water-soluble sugar alcohol", the term "water-soluble sugar alcohol" as used herein means ingredients other than δ-mannitol. Preferable examples of the "water-soluble sugar alcohol" include xylitol and erythritol. Erythritol is conventionally produced by fermentation of glucose as a raw material with yeast or the like. In the present invention, erythritol having a particle size of 50 mesh or less is used. The erythritol is commercially available (Nikken Chemicals Co., Ltd., etc.).

The amount of the "water-soluble sugar alcohol" used in addition to the δ-mannitol is usually about 3 to 50 parts by weight, preferably about 5 to 30 parts by weight based on 100 parts by weight of a total preparation.

The "crystalline cellulose" may be obtained by partial depolymerization of α-cellulose followed by purification. The "crystalline cellulose" also includes microcrystalline cellulose. Specific examples of the crystalline cellulose include Ceolus KG 801, Ceolus KG 802, Avicel PH 101, Avicel PH 102, Avicel PH 301, Avicel PH 302, Avicel RC-591 (crystalline cellulose/carmellose sodium) and the like. Preferred is so-called high-compatible Avicel including Ceolus KG 801 and Ceolus KG 802. These crystalline celluloses may be used alone, or two or more kinds may be used in combination. These crystalline celluloses are commercially available (Asahi Kasei Corporation).

The crystalline cellulose may be incorporated in an amount of about 3 to 50 parts by weight, preferably about 5 to 40 parts by weight, most preferably about 5 to 20 parts by weight into 100 parts by weight of a total preparation.

The "low-substituted hydroxypropyl cellulose" means a low-substituted hydroxypropyl cellulose having a hydroxypropoxyl group content (hereinafter, abbreviated as "an HPC group content" in some cases) of about 5.0 to 9.9% by weight, inter alia, a low-substituted hydroxypropyl cellulose having an HPC group content of about 5.0 to 7.0% by weight, a low-substituted hydroxypropyl cellulose having an HPC group content of about 7.0 to 9.9% by weight, and the like.

Examples of the low-substituted hydroxypropyl cellulose having an HPC group content of about 7.0 to 9.9% include LH-22, LH-32 and a mixture thereof, and these are commercially available (Shin-Etsu Chemical Co., Ltd.). Examples of the low-substituted hydroxypropyl cellulose having an HPC group content of about 5.0 to 7.0% include LH-23, LH-33 and a mixture thereof.

The particle diameter of the "low-substituted hydroxypropyl cellulose having a hydroxypropoxyl group content of 5.0 to 7.0% by weight" used in the present invention is for example about 5 to 60 μm, preferably about 10 to 40 μm as the average particle diameter.

Within such a range, when L-HPC having a relatively large particle diameter (e.g. L-HPC having an average particle diameter of about 26 to 40 μm) is used, a preparation having an excellent disintegrating property can be produced. On the other hand, when L-HPC having a relatively small particle diameter (e.g. L-HPC having an average particle diameter of about 10 to 25 μm) is used, a preparation having an excellent strength can be produced. Therefore, the particle diameter of L-HPC can be appropriately selected depending on the desired preparation properties.

The low-substituted hydroxypropyl cellulose having an HPC group content of 5.0 to 7.0% by weight or the low-substituted hydroxypropyl cellulose having an HPC group content of 7.0 to 9.9% is used in an amount of usually about 1 to 50 parts by weight, preferably about 1 to 40 parts by weight, further preferably 1 to 20 parts by weight based on 100 parts by weight of a total preparation, in order to obtain a preparation having a sufficient orally disintegrating property and a sufficient strength.

Examples of the binder include hydroxypropyl cellulose, hydroxypropyl methylcellulose, crystalline cellulose, gelatinized starch, polyvinylpyrrolidone, gum arabic powder, gelatin, pullulan, and the like. Two or more kinds of these binders may be used as a mixture at an appropriate ratio. When crystalline cellulose is used as the binder, a solid preparation having a higher strength and retaining an excellent orally rapidly disintegrating property can be obtained. The crystalline cellulose may be obtained by partial depolymerization of α-cellulose followed by purification. The "crystalline cellulose" also includes a cellulose referred to as microcrystalline cellulose. Specific examples of the crystalline cellulose include Ceolus KG 801, Ceolus KG 802, Avicel PH 101, Avicel PH 102, Avicel PH 301, Avicel PH 302, Avicel RC-591 (crystalline cellulose/carmellose sodium) and the like. Preferred is so-called high-compatible Avicel including Ceolus KG 801 and Ceolus KG 802. These crystalline celluloses may be used alone, or two or more kinds may be used in combination. These crystalline celluloses are commercially available (Asahi Kasei Corporation). In the case of a solid preparation not containing microgranules, the crystalline cellulose is used in an amount of for example 1 to 50 parts by weight, preferably 2 to 40 parts by weight, further preferably 2 to 20 parts by weight based on 100 parts by weight of the total preparation.

Examples of the acidulant include citric acid (anhydrous citric acid), tartaric acid, malic acid and the like.

Examples of the effervescent agent include sodium bicarbonate and the like.

Examples of the artificial sweetener include saccharine sodium, dipotassium glycyrrhizinate, aspartame, stevia, thaumatin and the like.

The flavor may be synthetic or natural, and examples thereof include lemon, lemon lime, orange, menthol, strawberry and the like.

Examples of the lubricant include magnesium stearate, a sucrose fatty acid ester, polyethylene glycol, talc, stearic acid and the like. When polyethylene glycol is used as the lubricant, a stable solid preparation in which degradation with time of an active pharmaceutical ingredient is suppressed can be obtained. In this case, polyethylene glycol is used in an amount of for example 0.01 to 10 parts by weight, preferably 0.1 to 5 parts by weight based on 100 parts by weight of the total preparation.

Examples of the colorant include edible dyes such as food Yellow No. 5, food Red No. 2, and food Blue No. 2; an edible lake dye, ferric oxide and the like.

Examples of the stabilizing agent include a basic substance in the case of a basic active pharmaceutical ingredient, and an acidic substance in the case of an acidic active pharmaceutical ingredient.

Examples of the excipient include lactose, white sugar, D-mannitol (β-D-mannitol, etc.), starch, corn starch, crystalline cellulose, light anhydrous silicic acid, titanium oxide and the like.

Examples of the disintegrant include so-called super disintegrants such as crospovidone [manufactured by ISP Inc. (USA), or BASF (Germany)], croscarmellose sodium (FMC-Asahi Kasei Corporation) and carmellose calcium (GO-TOKU CHEMICAL COMPANY LTD.); hydroxypropyl cellulose, low-substituted hydroxypropyl cellulose; carboxymethyl starch sodium (Matsutani Chemical Industry Co., Ltd.); corn starch, and the like. Among them, crospovidone is preferably used. Two or more kinds of these disintegrants may be used as a mixture at an appropriate ratio.

The crospovidone may be any crosslinked polymer referred to as 1-ethenyl-2-pyrrolidinone homopolymer, including polyvinyl polypyrrolidone (PVPP) and 1-vinyl-2-pyrrolidinone homopolymers, and usually, the crospovidone having a molecular weight of 1,000,000 or more is used. Specific examples of commercially available crospovidone include crosslinked povidone, Kollidon CL [manufactured by BASF (Germany)], Polyplasdone XL, Polyplasdone XL-10, INF-[manufactured by ISP Inc. (USA)], polyvinylpyrrolidone, PVPP, 1-vinyl-2-pyrrolidinone homopolymers and the like.

These disintegrants may be used alone, or two or more kinds of them may be used in combination. For example, crospovidone may be used alone or in combination with other disintegrants.

The disintegrant is used in an amount of for example 0.1 to 20 parts by weight, preferably 1 to 10 parts by weight, further preferably 3 to 7 parts by weight based on 100 parts by weight of a total preparation.

Examples of the dosage form of the orally disintegrating solid preparation of the present invention include a tablet, a granule, a microgranule and the like. Among them, preferred is a tablet (an orally disintegrating tablet, a disintegrating tablet in water). Particularly preferred is an orally rapidly disintegrating tablet.

When the active pharmaceutical ingredient is an acid-labile active pharmaceutical ingredient such as lansoprazole, omeprazole, rabeprazole, pantoprazole, ilaprazole or tenatoprazole, it is preferable that a basic inorganic salt is incorporated into a preparation in order to stabilize the active pharmaceutical ingredient in the preparation. Examples of the basic inorganic salt include basic inorganic salts of sodium, potassium, magnesium and/or calcium. Preferred are basic inorganic salts of magnesium and/or calcium. Particularly preferred is a basic inorganic salt of magnesium.

Examples of the basic inorganic salt of sodium include sodium carbonate, sodium hydrogen carbonate, sodium phosphate, disodium hydrogen phosphate and the like.

Examples of the basic inorganic salt of potassium include potassium carbonate, potassium hydrogen carbonate, sodium potassium carbonate, potassium phosphate, dipotassium hydrogen phosphate and the like.

Examples of the basic inorganic salt of magnesium include heavy magnesium carbonate, magnesium carbonate, magnesium oxide, magnesium hydroxide, magnesium aluminate metasilicate, magnesium aluminate silicate, magnesium silicate, magnesium aluminate, synthetic hydrotalcite [$Mg_6Al_2(OH)_{16}.CO_3.4H_2O$] and aluminium/magnesium hydroxide ($2.5MgO.Al_2O_3.H_2O$). Among them, preferred are heavy magnesium carbonate, magnesium carbonate, magnesium oxide, magnesium hydroxide and the like.

Examples of the basic inorganic salt of calcium include precipitated calcium carbonate, calcium hydroxide and the like.

The basic inorganic salt is preferably a basic inorganic salt of magnesium, and further preferably, heavy magnesium carbonate, magnesium carbonate, magnesium oxide, or magnesium hydroxide.

The basic inorganic salt of magnesium, calcium or the like may be a 1% aqueous solution or suspension thereof having a basic pH (pH 7 or higher).

Two or more kinds of these basic inorganic salts (preferably, magnesium salt and calcium salt, etc.) may be used a mixture at an appropriate ratio.

The use amount of the basic inorganic salt may be appropriately selected depending on the kind of the basic inorganic salt. The use amount of the basic inorganic salt is for example 0.3 to 200% by weight, preferably 1 to 100% by weight, further preferably 10 to 50% by weight, most preferably 20 to 40% by weight of the active pharmaceutical ingredient.

As described above, the orally disintegrating solid preparation of the present invention may be in any form of a tablet, a granule, a microgranule and the like. When the orally disintegrating solid preparation of the present invention is a tablet, the tablet may contain microgranules. The microgranule may contain the active pharmaceutical ingredient. These dosage forms can be produced by a known method or a similar method thereof.

The microgranule may contain a core containing or not containing the active pharmaceutical ingredient. Examples of such a core include (1) a spherical granule of crystalline cellulose and lactose [e.g. a spherical granule having a size of about 100 to 200 μm produced from crystalline cellulose (3 parts) and lactose (7 parts) (Nonpareil 105 (trade name), manufactured by Freund); a spherical granule having a size of about 150 to 250 μm produced from crystalline cellulose (3 parts) and lactose (7 parts) (Nonpareil NP-7:3 (trade name), manufactured by Freund); a spherical granule having a size of about 150 to 250 μm produced from crystalline cellulose (5 parts) and lactose (5 parts) (Nonpareil NP-5:5 (trade name), manufactured by Freund)], (2) a spherical granule having a size of about 150 to 250 μm of crystalline cellulose [Avicel SP (trade name), manufactured by Asahi Kasei Corporation], and the like.

The core may be coated with the active pharmaceutical ingredient or the like, and then further coated for the purpose of masking of a taste and an odor, or providing an enteric coating or a sustained-release property by a known method. In this case, the core is a microgranule containing the active pharmaceutical ingredient. In this case, examples of a coating agent include an aqueous enteric polymer base used for the purpose of forming an enteric coating layer, such as cellulose acetate phthalate (CAP), hypromellose phthalate (hereinafter, described as HP-55), hydroxymethylcellulose acetate succinate, a methacrylic acid copolymer [e.g. Eudragit L30D-55 (trade name; manufactured by ROEHM), Kollicoat MAE30DP (trade name; manufactured by BASF), Polykid PA30 (trade name; manufactured by Sanyo Chemical Industries, Ltd.), etc.], carboxymethylethylcellulose, and shellac; a sustained-release base such as a methacrylic acid copolymer [e.g. Eudragit NE30D (trade name), Eudragit RL30D (trade name), Eudragit RS30D (trade name), etc.]; a water-soluble polymer; a plasticizer such as triethyl citrate, polyethylene glycol, acetylated monoglyceride, triacetin, and castor oil, and the like. These coating agents may be used alone or as a mixture of two or more kinds.

The enteric coating layer is preferably formed from an aqueous enteric polymer base and a sustained-release base, if necessary, in combination with a plasticizer.

The aqueous enteric polymer base is preferably a methacrylic acid copolymer.

The sustained-release base is preferably a methacrylic acid copolymer.

The use amount of the sustained-release base is about 5 to 30% by weight, preferably about 5 to 15% by weight based on 100% by weight of the aqueous enteric polymer base. The preferable use amount of the plasticizer is 5 to 30% by weight based on 100% by weight of the aqueous enteric polymer base.

The "microgranule" can be also produced by a known granulation method.

Examples of the "granulation method" include a rotating granulation method (e.g. centrifugation tumbling granulation method), a fluidized granulation method (e.g. rotating fluidized bed granulation, fluidized granulation, etc.), an agitation granulation method and the like. Among them, a fluidized granulation method is preferred. Particularly preferred is a rotating fluidized bed granulation method.

Specific examples of a rotating granulation method include a method using a "CF apparatus" manufactured by Freund and the like. Specific examples of a rotating fluidized bed granulation method include methods using "SPIR-A-FLOW", "Multiplex" manufactured by Powlex, "Newmarume" manufactured by Fuji Paudal Co., Ltd. and the like. A method of spraying a mixture can be appropriately selected depending on the kind of a granulation apparatus and, for example, it may be any of a top spraying manner, a bottom spraying manner and a tangential spraying manner. Among them, a tangential spraying manner is preferred.

The "microgranule" can be coated with an ingredient including the active pharmaceutical ingredient other than ingredients of the microgranule by a per se known method or a similar method thereof. For example, when the active pharmaceutical ingredient is an acid-labile physiologically active substance, a core containing crystalline cellulose and lactose may be coated with the acid-labile physiologically active substance.

For example, a production method (coating method) described in JP-A 5-092918 may be used, and the method comprises coating a core containing crystalline cellulose and lactose with an acid-labile physiologically active substance, and if necessary, a basic inorganic salt, a binder, a lubricant, an excipient, a water-soluble polymer or the like (hereinafter, abbreviated as a coating layer in some cases). For example, a core is coated with an acid-labile physiologically active substance and a basic inorganic salt, and then coated with a binder, a lubricant, an excipient, a water-soluble polymer or the like.

Examples of the basic inorganic salt, the binder, the lubricant and the excipient that may be used include those described above. Examples of the "water-soluble polymer" that may be used include an ethanol-soluble water-soluble polymer [e.g. a cellulose derivative such as hydroxypropyl cellulose (hereinafter, referred to as HPC in some cases) polyvinylpyrrolidone, etc.], an ethanol-insoluble water-soluble polymer [e.g. a cellulose derivative such as hypromellose (hereinafter, referred to as HPMC in some cases), methylcellulose, or carboxymethylcellulose sodium, sodium polyacrylate, polyvinyl alcohol, sodium alginate, guar gum, etc.] and the like.

The average particle diameter of the "core" may be 250 µm or less, preferably 50 to 250 µm, more preferably 100 to 250 µm, particularly preferably 100 to 200 µm. The cores having the above-described average particle diameter include particles all of which pass through a No. 50 (300 µm) sieve, about 5 w/w % or less of which remain on a No. 60 (250 µm) sieve, and about 10 w/w % or less of which pass through a No. 282 (53 µm) sieve. The specific volume of the "core" is 5 ml/g or less, preferably 3 ml/g or less.

Examples of the "core" include (1) a spherical granule of crystalline cellulose and lactose, (2) a spherical granule having a size of 150 to 250 µm of crystalline cellulose (manufactured by Asahi Kasei Corporation, Avicel SP), (3) a granule having a size of 50 to 250 µm produced from lactose (9 parts) and α-starch (1 part) by stirring granulation, (4) a micro particle having a size of 250 µm or smaller obtained by classification of microcrystalline cellulose spherical granules described in JP-A 61-213201, (5) a processed product of wax which is formed into a sphere by spray chilling or melt granulation, (6) a processed product such as a gelatin bead comprising an oil ingredient, (7) calcium silicate, (8) starch, (9) a porous particle such as chitin, cellulose, chitosan or the like, (10) a bulk powder of granulated sugar, crystalline lactose, crystalline cellulose, sodium chloride or the like, and a processed preparation thereof. Further, these cores may be produced by a per se known grinding method or granulation method, and then sieved to prepare particles having the desired particle diameter.

Examples of the "spherical granule of crystalline cellulose and lactose" include (i) a spherical granule having a size of 100 to 200 µm produced from crystalline cellulose (3 parts) and lactose (7 parts) (e.g. Nonpareil 105 (70-140) (particle diameter: 100 to 200 µm), manufactured by Freund), (ii) a spherical granule having a size of 150 to 250 µm produced from crystalline cellulose (3 parts) and lactose (7 parts) (e.g. Nonpareil NP-7:3, manufactured by Freund), (iii) a spherical granule having a size of 100 to 200 µm produced from crystalline cellulose (4.5 parts) and lactose (5.5 parts) (e.g. Nonpareil 105T (70-140) (particle diameter: 100 to 200 µm), manufactured by Freund), (iv) a spherical granule having a size of 150 to 250 µm produced from crystalline cellulose (5 parts) and lactose (5 parts) (e.g. Nonpareil NP-5:5, manufactured by Freund) and the like.

In order to produce a preparation retaining a suitable strength and having excellent solubility, the "core" is preferably a spherical granule of crystalline cellulose and lactose, and more preferably a spherical granule of crystalline cellulose and lactose which contains 50% by weight or more of lactose. Preferred is a granule containing 40 to 50% by weight of crystalline cellulose and 50 to 60% by weight of lactose.

The core used in the present invention is preferably a spherical granule of crystalline cellulose and lactose, and further preferably a spherical granule having a size of 100 to 200 µm produced from crystalline cellulose (4.5 parts) and lactose (5.5 parts).

The "core" may contain a physiologically active substance such as the active pharmaceutical ingredient as described above. However, release of the physiologically active substance can be controlled by a coating layer containing the physiologically active substance, and therefore the core may not contain the physiologically active substance.

The "core" may be in the form of a microgranule. In order to reduce variation in the coating amount, it is preferable that the core is as uniform spherical as possible.

The ratio of the "coating layer" to the "core" can be selected in such a range that dissolution of the physiologically active substance and the particle size of a composition can be controlled. For example, the ratio is usually 50 to 400 parts by weight of the coating layer to 100 parts by weight of the core.

The "coating layer" may comprise a plurality of layers, and at least one layer of the coating layers may contain the physiologically active substance. A combination of various coating layers including a coating layer not containing the active pharmaceutical ingredient, a coating layer for undercoating and an enteric coating layer may be appropriately selected.

When the core is coated, for example, a mixture of the physiologically active substance and the water-soluble polymer is used. The mixture may be a solution or a dispersion, and can be prepared using water or an organic solvent such as ethanol, or a mixture thereof.

The concentration of the water-soluble polymer in the mixture is varied depending on the addition amounts of the physiologically active substance and an additive so that the binding ability of the physiologically active substance to the core can be retained and the viscosity of the mixture can be maintained without reducing workability, and it is usually 0.1 to 50% by weight, preferably 0.5 to 10% by weight.

When the coating layer comprises a plurality of layers, the concentration of the physiologically active substance in each layer may be changed successively or gradually by selecting the content of the water-soluble polymer or the viscosity grade of a mixture or by coating successively using mixtures which are different in the proportions of the physiologically active substance and the other additives in the mixtures. In this case, coating may be performed using a mixture containing the water-soluble polymer in an amount out of the range of 0.1 to 50% by weight, as long as coating layers in total contain 0.1 to 50% by weight of the water-soluble polymer. Further, the coating layer comprising a plurality of layers may comprise inert film layers formed by a known method so that the inert film layer can block each layer containing the physiologically active substance.

When two or more kinds of physiologically active substances which are incompatible are used, the core may be coated with each mixture of each physiologically active substance together or separately.

The coated core is dried, and then passed through a sieve to obtain a composition having uniform particle size. The shape of the composition usually corresponds to the core, and thus a nearly spherical composition can be obtained. As the sieve, for example, a No. 50 (300 µm) round sieve can be used. The composition is obtained by selecting from particles which pass through the No. 50 round sieve.

The "microgranule" is produced by coating a composition with an enteric coating layer for the purpose of protecting the physiologically active substance or imparting enteric dissolution, in accordance with the same manner as the aforementioned granulation method. If necessary, the microgranule may be further coated with a water-soluble sugar alcohol (preferably, mannitol such as β-mannitol). When coated with a water-soluble sugar alcohol, the strength of an orally disintegrating tablet containing the microgranules is improved.

The enteric coating layer comprises, for example, a combination of the aqueous enteric polymer base, the sustained-release base, the plasticizer and the like as described above, and is preferably a layer having a thickness of 20 to 70 µm, preferably 30 to 50 µm and coating the whole surface of a composition containing the physiologically active substance. Therefore, when the particle diameter of the composition is smaller, the weight percent of the enteric coating layer in the whole microgranules is higher. In the microgranule of the present invention, the enteric coating layer is 30 to 70% by weight, preferably 50 to 70% by weight of the whole microgranules.

The enteric coating layer may be composed of a plurality of layers (e.g. 2 to 3 layers). An example of a coating method comprises coating a composition with an enteric coating layer containing polyethylene glycol, with an enteric coating layer containing triethyl citrate, and then with an enteric coating layer containing polyethylene glycol.

The orally disintegrating solid preparation of the present invention is produced by a method conventionally used in the pharmaceutical field. An example of such a method is a method comprising mixing an active pharmaceutical ingredient, δ-mannitol and, if necessary, crystalline cellulose and/or low-substituted hydroxypropyl cellulose, and other additives, contacting the mixture with a predetermined amount of an aqueous solvent (e.g. water; lower alcohol such as methanol or ethanol; acetone; or a mixed solvent thereof, preferably water), and then drying the mixture. Molding can be performed by a conventional method before or after drying the mixture, or molding may be performed during drying the mixture.

When a δ-mannitol crystal is contacted with an aqueous solvent, crystal transformation into β-form occurs at the contacting surface, which contributes to improvement in the hardness of a preparation. In the production method of the present invention, it is important that δ-mannitol is contacted with an aqueous solvent, whereby crystal transformation from δ-form into β-form is induced.

The contact of δ-mannitol with an aqueous solvent can be performed by dissolving, suspending or immersing δ-mannitol in the aqueous solvent.

A method of contacting δ-mannitol with an aqueous solvent is not particularly limited, and it may comprise mixing an aqueous solvent and δ-mannitol under stirring, or spraying or adding dropwise an aqueous solvent to δ-mannitol under stirring. Another contacting method may comprise contacting of δ-mannitol under the environment containing the steam of an aqueous solvent at a high concentration (e.g. under high humidity environment).

The crystal surface or interior of δ-mannitol used as a raw material can be transformed from δ-form to fine β-form by treating the δ-mannitol with an aqueous solvent followed by drying (preferably rapidly drying). More specifically, the surface of the δ-mannitol is wetted with an aqueous solvent, and thereby a part or all of the δ-crystals which are reacted with the solvent are sequentially transformed into β-crystal from the crystal surface toward the interior. Then, growth of the resulting β-crystals is suppressed by drying. Thus, a compact interior structure of pharmaceutical ingredients can be constructed. Therefore, a preparation obtained by the production method of the present invention usually exists as a mixture of the δ-crystals and the β-crystals. The ratio of the δ-crystals and the β-crystals in the mixture is determined by the crystal transformation step and the crystal growth suppression step as described above, and it is not particularly limited.

The "orally disintegrating solid preparation comprising microgranules" is appropriately produced using an appropriate active pharmaceutical ingredient selected from the aforementioned physiologically active substances by a conventional molding method.

For example, the orally disintegrating solid preparation of the present invention can be produced by mixing the "microgranules containing an active pharmaceutical ingredient" and an additive containing δ-mannitol and then tableting the mixture. In addition, as described above, it is important that the production method of the present invention comprises a step of contacting δ-mannitol with an aqueous solvent.

Examples of the "microgranule containing an active pharmaceutical ingredient" include the "microgranule containing a coated core" and the like.

An example of a method of producing an orally disintegrating tablet using the "additive containing δ-mannitol" and the "microgranule containing a coated core" will be shown below.

The "additive containing δ-mannitol" may contain crystalline cellulose and/or low-substituted hydroxypropyl cellulose and, further if necessary, may contain the above-exemplified various additives such as a binder, an acidulant, an effervescent agent, an artificial sweetener, a flavor, a lubricant, a colorant, a stabilizing agent, an excipient, and a disintegrant.

The crystalline cellulose may be present in the orally disintegrating tablet in an amount of about 3 to 50 parts by weight, preferably about 5 to 40 parts by weight, most preferably about 5 to 20 parts by weight based on 100 parts by weight of ingredients other than the microgranules of the orally disintegrating tablet.

The low-substituted hydroxypropyl cellulose, for example, a low-substituted hydroxypropyl cellulose having an HPC group content of 5.0 to 7.0% by weight or a low-substituted hydroxypropyl cellulose having an HPC group content of 7.0 to 9.9% is used usually in an amount of about 3 to 50 parts by weight, preferably about 5 to 40 parts by weight, further preferably 5 to 20 parts by weight based on 100 parts by weight of ingredients other than the microgranules of the orally disintegrating tablet, in order to provide sufficient oral disintegrating property and sufficient preparation strength.

The "additive containing δ-mannitol" may be used as mixed powder of the aforementioned various additives, or may be granulated by a conventional granulation method.

A granulation means is not particularly limited, and for example, a per se known dry granulation method; a wet granulation method such as agitation granulation, extrusion granulation, fluidized bed granulation and rotating granulation, or a spraying method can be used.

A dry granulation method comprises steps of strongly compressing raw material powder as it is or as a mixture with the aforementioned suitable binder and the like into a small mass, suitably grinding the small mass, and then granulating the ground mass. In the case of using a dry granulation method, δ-mannitol can not be sufficiently contacted with an aqueous solvent, and thus the crystal transformation from δ-mannitol to β-mannitol is difficult. Therefore, the desired effect is hardly obtained.

A wet granulation method comprises steps of mixing raw material powder with a solution or a suspension of the aforementioned suitable binder and the like, and then subjecting the mixture to granulation, drying, and size-adjustment. Wetted raw material powder may be rotated by vibration or rotation movement to obtain compact spherical particles.

A spraying method comprises steps of spraying raw material slurry as fine liquid droplets with a nozzle or a rotation disc and then drying the droplets with hot air.

As used herein, an extrusion granulation refers to a method comprising mixing a mixture of an active pharmaceutical ingredient and an additive or only an active pharmaceutical ingredient with a solvent, and then extruding the mixture through a screen or a die by a pressure applied with a screw or a roller.

As used herein, an agitation granulation refers to a method comprising putting solid materials such as an active pharmaceutical ingredient or a mixture of an active pharmaceutical ingredient and an additive into an agitation granulator (e.g. vertical granulator, pony mixer, etc.), and granulating the materials by kneading while an aqueous solution or suspension containing a binder and the like is added.

As used herein, a fluidized bed granulation refers to a method comprising spraying a solution or suspension containing a binder and the like onto an active pharmaceutical ingredient or a mixture of an active pharmaceutical ingredient and an additive which is retained in a fluidized state, thereby agglomerating powders with the binder and then granulating the agglomerate.

As used herein, a rotating granulation refers to a method comprising rotating raw material powder by the action of stirring wings in a pan-type, drum-type or vibration-type container while an aqueous solution or suspension containing a binder and the like is sprayed, thereby producing fine grains by crosslinking formation between particles, and then promoting growth of the grains by subjecting them to tumbling and/or rotation movement.

When an additive containing δ-mannitol is granulated, it is preferable to use a wet granulation method such as an agitation granulation method or a fluidized bed granulation method. It is particularly preferable to use a fluidized bed granulation method.

When an agitation granulation method is used, a dry granulated product can be obtained, for example, by putting δ-mannitol and, if necessary, crystalline cellulose and/or low-substituted hydroxypropyl cellulose and other additives (e.g. the above-exemplified binder, acidulant, effervescent agent, artificial sweetener, flavor, lubricant, colorant, stabilizing agent, excipient, disintegrant, etc.) as solid materials into an agitation granulator (e.g. vertical granulator, pony mixer, etc.), kneading the materials while a solution (preferably, aqueous solution) or suspension of δ-mannitol and/or a binder in an aqueous solvent (e.g. water; lower alcohol such as methanol or ethanol; acetone; or mixed solvent of them) is added, and then drying.

The agitation granulation comprises a step of adding a solution containing δ-mannitol and/or a binder and the like to an additive composition which is put as a solid material into a granulator, a kneading step and a drying step.

In the step of adding a solution containing δ-mannitol and/or a binder and the like to an additive composition which is put as a solid material into a granulator, it is preferable that the solution containing a binder and the like is added in an amount of about 2 to about 10% by weight based on the total amount of the additive composition at an addition rate of about 300 to about 3000 g/min (preferably, about 500 to about 2500 g/min). For example, when a vertical granulator is used in kneading, about 120 kg of the solid material may be kneaded at a rotation number of about 100 to about 500 rpm, preferably about 200 rpm, for a kneading time of about 3 to about 30 minutes, preferably about 5 to about 15 minutes. When a pony mixer is used, the same amount of the solid material may be kneaded for about 3 to about 60 minutes, preferably about 15 to about 30 minutes. The endpoint of kneading may be determined by power consumption.

For an agitation granulation method, examples of a solution containing δ-mannitol and/or a binder and the like, and an additive composition to be put as a solid material into a granulator are shown below.

[Solution Containing δ-Mannitol and the Like]

EXAMPLE

δ-mannitol: about 10 to about 100 parts by weight based on the total amount of solutes in a solution
Water: about 6 to about 20 parts by weight per 1 part by weight of δ-mannitol

[Additive Composition to be Put as a Solid Material]

Example 1

δ-mannitol: about 5 to about 98 parts by weight based on the total amount of additives put as solid materials
Crystalline cellulose: about 1 to about 50 parts by weight based on the total amount of additives put as solid materials
Low-substituted hydroxypropyl cellulose: about 1 to about 50 parts by weight based on the total amount of additives put as solid materials Example 2

δ-mannitol: about 5 to about 98 parts by weight based on the total amount of additives put as solid materials
Crystalline cellulose: about 1 to about 50 parts by weight based on the total amount of additives put as solid materials
Low-substituted hydroxypropyl cellulose: about 1 to about 50 parts by weight based on the total amount of additives put as solid materials
Disintegrant (e.g. crospovidone, etc.): about 0.1 to about 20 parts by weight based on the total amount of additives put as solid materials When a fluidized bed granulation method is used, dried powder can be obtained, for example, by putting δ-mannitol and, if necessary, crystalline cellulose and/or low-substituted hydroxypropyl cellulose and other additives (e.g. the above-exemplified binder, acidulant, effervescent agent, artificial sweetener, flavor, lubricant, colorant, stabilizing agent, excipient, disintegrant, etc.) as solid materials into a fluidized bed granulator, spraying a solution (preferably, aqueous solution) or suspension of δ-mannitol and/or a binder and the like in an aqueous solvent (e.g. water; lower alcohol such as methanol or ethanol; acetone; mixed solvent of them), and then drying.

The fluidized bed granulation comprises a step of spraying a solution containing δ-mannitol and/or a binder and the like to an additive composition which is put as a solid material into a granulator, and a drying step.

In the spraying step, it is preferable that a solution containing δ-mannitol and/or a binder and the like is sprayed in an amount of about 2 to about 10% by weight as a spraying additive based on the total amount of additives at a supplying rate of about 300 to about 3000 g/min (preferably, about 500 to about 2500 g/min).

The fluidization condition during the spraying step is a supply air temperature of about 60 to about 120° C. (preferably, about 70 to about 110° C.) and a supply air amount of about 5 to about 70 m$^3$/min (preferably, about 10 to about 60 m$^3$/min).

For the step of spraying a solution containing δ-mannitol and/or a binder and the like onto δ-mannitol and, if necessary, crystalline cellulose and/or low-substituted hydroxypropyl cellulose and other additives in a fluidized bed granulation method, composition of raw materials to be sprayed and composition of solid materials to be put into a granulator are exemplified. This is merely one example and, further, the aforementioned binder, acidulant, effervescent agent, artificial sweetener, flavor, lubricant, colorant, stabilizing agent, excipient, disintegrant and the like may be contained in the composition if necessary.

For a fluidized bed granulation method, examples of the solution containing δ-mannitol and the like and the additive composition to be put as a solid material into a granulator are shown below.

[Solution Containing δ-Mannitol and the Like]

Example

δ-mannitol: about 10 to about 100 parts by weight based on the total amount of solutes in a solution
Water: about 6 to about 20 parts by weight per 1 part by weight of δ-mannitol

[Additive Composition to be Put as a Solid Material]

Example 1

δ-mannitol: about 5 to about 98 parts by weight based on the total amount of additives put as solid materials
Crystalline cellulose: about 1 to about 50 parts by weight based on the total amount of additives put as solid materials
Low-substituted hydroxypropyl cellulose: about 1 to about 50 parts by weight based on the total amount of additives put as solid materials Example 2

δ-mannitol: about 5 to about 98 parts by weight based on the total amount of additives put as solid materials
Crystalline cellulose: about 1 to about 50 parts by weight based on the total amount of additives put as solid materials
Low-substituted hydroxypropyl cellulose: about 1 to about 50 parts by weight based on the total amount of additives put as solid materials
Disintegrant (e.g. crospovidone, etc.): about 0.1 to about 20 parts by weight based on the total amount of additives put as solid materials After dried powder is produced by a fluidized bed granulation method or an agitation granulation method, the resulting dried powder of additives may be used as it is in a next step, or may be subjected to a size-adjustment step.

In a drying step of a fluidized bed granulation method or an agitation granulation method, it is important to control moisture during granulation. The moisture during granulation can be confirmed by equilibrium relative humidity (ERH) as an index. An equilibrium relative humidity is generally used as an index of the moisture amount in an environment, and indicates a humidity at which a substance or a composition placed under a certain relative humidity (under a humidity environment) reaches equilibrium. An equilibrium relative humidity is also used as an index of the moisture content in a substance or a composition, and means a value 100 times the so-called moisture activity (Aw). Herein, Aw means mobile water (see Pharmaceutical Research, Vol. 8, No. 3, 1991 (p 292-p 297), D. R. Heidemann and P. J. Jarosz). The equilibrium relative humidity can be measured, for example, with a Rotronic water activity measuring apparatus (manufactured by Rotronic AG), which it is not limited to.

In the production method of the present invention, when the "additive containing δ-mannitol" is granulated, it is preferable that an ERH during granulation is a high moisture level of about 70 to 100%.

Conditions for drying vary depending on a preparation to be dried. For example, in the case of vacuum drying, drying may be performed at about 40° C. for about 10 about 20 hours. In the case of fluidized bed drying, drying can be performed under the conditions of an air supply amount of about 30 about 60 Nm$^3$/min, an air supply temperature of about 80 to 100° C., and an exhaust air temperature of about 40 to about 60° C. after completion of drying.

The "microgranule containing a coated core" can be produced, for example, by coating a core containing crystalline cellulose and lactose with a physiologically active substance and an excipient and further with a coating layer containing a water-soluble polymer to obtain a composition, coating the resulting composition with an enteric coating layer containing polyethylene glycol, an enteric coating layer containing triethyl citrate, an enteric coating layer containing polyethylene glycol and further with mannitol (this may be β-mannitol or δ-mannitol, or a mixture thereof) to obtain a microgranule, mixing the resulting microgranule with an additive containing δ-mannitol, and then molding the mixture.

For example, when the orally disintegrating solid preparation is a tablet (i.e. orally disintegrating tablet), "molding" can be performed by tableting at a pressure of 0.5 to 3 ton/cm$^2$, preferably 1 to 2 ton/cm$^2$, using a single tableting machine (manufactured by Kikusui Seisakusho-Ltd.) or a rotary tableting machine (manufactured by Kikusui Seisakusho Ltd.).

"Drying" may be performed by any method used for generally drying a preparation, such as vacuum drying or fluidized bed drying.

It is desirable that the dry state of the orally disintegrating solid preparation of the present invention is maintained at an ERH of 30% or less.

Mixing is performed by a generally used mixing method such as mixing, kneading, granulation and the like. Mixing is performed using an apparatus such as a vertical granulator VG10 (manufactured by Powlex), a universal kneader (manufactured by Hata Iron works Co., Ltd), a fluidized bed granulator LAB-1 or FD-3S (manufactured by Powlex), or a rotating fluidized bed granulator MP-10 or MP-400 (manufactured by Powlex).

The orally disintegrating solid preparation of the present invention can be produced by mixing the granulated additive containing δ-mannitol as described above, microgranules containing a coated core and, if necessary, other additives and then tableting the mixture.

A tableting method is not particularly limited. For example, tableting can be performed according to a method described in JP-A 2003-081814. Preferably tableting is performed at a tableting temperature of about 25° C. to about 60° C.

As used herein, the "coating" means not only coating of the whole surface of a subject to be coated (e.g. core) but also partial coating of the subject surface or adsorption or absorption on the subject surface.

As used herein, the "spherical" means not only a true sphere but also a shape having a curved surface such as an ellipse in cross-section, an eggplant-like shape, or a droplet-like shape.

The "average particle diameter" means a volume median diameter (median diameter: a particle diameter corresponding to 50% of cumulative distribution). Examples of a method of measuring the average particle diameter include a laser diffraction particle size distribution measuring method, specifically, a method using a laser diffraction particle size distribution analyzer HEROS RODOS (manufactured by Sympatec, Germany).

The "microgranule" in the present invention has an average particle diameter of preferably 400 μm or less, further preferably 300 to 400 μm so as not to induce a rough feeling or an uncomfortable feeling in the mouth.

When not the average particle diameter but the maximum particle size of the "microgranule" is defined, the microgranule has a particle diameter of substantially 425 μm or less, preferably substantially 400 μm or less. The particle diameter of the microgranule is preferably in a range of substantially 300 to 425 μm, further preferably in a range of substantially 300 to 400 μm.

The "substantially" of the "particle diameter of substantially 425 μm or less" and the "particle diameter of substantially 400 μm or less" means that the microgranules may comprise a small amount (5% by weight or less) of particles having a particle diameter out of the above range which are inevitably mixed.

The "microgranule" may contain a hiding agent, for example, titanium oxide or the like.

When "orally disintegrating tablet" of the present invention has a diameter of 5 to 20 mm, preferably 7 to 15 mm, further preferably 8 to 13 mm, it is advantageous to handling and administration.

The orally disintegrating solid preparation of the present invention thus obtained rapidly disintegrates or dissolves in the oral cavity or in water and has a suitable strength. Further, the orally disintegrating solid preparation of the present invention has a pleasant mouthfeel in which a powdery mouthfeel is improved.

The oral disintegration time (a time until a solid preparation is completely disintegrated with saliva in the oral cavity of a healthy adult man or woman) of the orally disintegrating solid preparation of the present invention is usually within 90 seconds, preferably within 1 minute, more preferably 5 to 50 seconds, further preferably 5 to 40 seconds, particularly preferably 5 to 35 seconds.

The disintegration time in water of the rapidly disintegrating solid preparation of the present invention is usually within 90 seconds, preferably within 1 minute, more preferably 5 to 40 seconds, further preferably 5 to 30 seconds, particularly preferably 5 to 25 seconds.

The strength (a value measured with a tablet hardness tester) of the rapidly disintegrating solid preparation of the present invention is usually about 10 N to about 150 N (about 1 kg to about 15 kg).

The orally disintegrating solid preparation of the present invention is useful particularly as an orally disintegrating tablet, and is administered without water or together with water. Examples of an administration method include (1) a method comprising holding the preparation of the present invention in the mouth and not swallowing the preparation as it is, and then dissolving or disintegrating the preparation with a small amount of water or with saliva in the oral cavity without water and (2) a method comprising swallowing a preparation as it is together with water. Alternatively, the tablet of the present invention may be dissolved or disintegrated with water, and then be administered.

The orally disintegrating solid preparation (particularly, orally disintegrating tablet) of the present invention is advantageously used in the cases (a) where it is frequently necessary to administer a preparation without water, (b) where a preparation is administered to a patient who hardly swallows a tablet, and (c) where a preparation is administered to an elderly adult or a child whose throat may be blocked by a usual tablet, and the like.

The orally disintegrating solid preparation of the present invention can be orally and safely administered to a mammal (e.g. mouse, rat, rabbit, cat, dog, cow, horse, monkey, human, etc.).

A dose of the orally disintegrating solid preparation of the present invention varies depending on an active pharmaceutical ingredient, a subject to be administered, the kind of a disease and the like, and may be selected from such a range that the dose of an active pharmaceutical ingredient can be an effective amount.

For example, when the active pharmaceutical ingredient is lansoprazole, the orally disintegrating solid preparation of the present invention is useful for treatment and prevention of a peptic ulcer (e.g. stomach ulcer, duodenal ulcer, anastomomic ulcer, Zollinger-Ellinson syndrome, etc.), gastritis, reflux esophagitis and the like; elimination or assistance in elimination of *H. pylori*; suppression of upper gastrointestinal tract bleeding caused by peptic ulcer, acute stress ulcer or hemorrhagic gastritis; suppression of upper gastrointestinal tract bleeding caused by invasive stress (stress caused by major operation which requires central control after operation, or cerebrovascular disorder, head trauma, multiple organ failure or extensive burn which requires intensive care); treatment and prevention of an ulcer caused by a non-steroidal antiinflammatory agent; treatment and prevention of gastric hyperacidity and an ulcer caused by postoperative stress; administration before anesthesia and the like. The dose of the orally disintegrating solid preparation of the present invention is 0.5 to 1500 mg/day, preferably 5 to 150 mg/day per adult (60 kg body weight) of lansoprazole.

Examples

Hereinafter, the present invention will be described in more detail with reference to Examples and Test Examples which the present invention is limited to.

Herein, % described below indicates % by weight unless otherwise is indicated.

The hardness of a tablet was measured by the following test method.

1) Hardness Test

A tablet hardness tester (manufactured by Toyama Sangyo Co., Ltd.) was used. The test was performed ten times, and the average of them is shown.

(1) Production of Coated Microgranules

Nonpareil 105 (trade name) (particle diameter: 100 to 200 μm) (41.58 kg) was put into a rotating fluidized bed granulator (manufactured by Powlex, Model MP-400) and coated by spraying a bulk solution of composition as described below, which was previously prepared, in a tangential spraying manner at a supply rate of 1.4 kg/min while the ventilation temperature was controlled so that the exhaust air temperature can be about 31° C. under steady state condition. When spraying of the predetermined amount 257.6 kg of the bulk solution was completed, the coated particles thus obtained were subsequently subjected to a step of the following (2) production of film-undercoated microgranules.
[Bulk Solution]

| | |
|---|---|
| Lansoprazole | 39.6 kg |
| Magnesium carbonate | 13.2 kg |
| Low-substituted hydroxypropyl cellulose LH-32 (hydroxypropoxyl group content: 8.8% by weight) | 6.6 kg |
| Hydroxypropyl cellulose (type SL) | 13.2 kg |
| Purified water | 185 L |

(2) Production of Film-Undercoated Microgranules

Subsequently to the above (1) production of coated microgranules, an undercoating film solution of composition as described below, which was previously prepared, was sprayed in a tangential spraying manner at a supply rate of 1.2 kg/min while the ventilation temperature was controlled so that the exhaust air temperature can be about 41° C. under steady state condition. When spraying of the predetermined amount 132.0 kg of the film solution was completed, spraying was stopped. The coated particles thus obtained were dried as they are for about 11 minutes, and then sieved through a No. 42 round sieve (350 μm) and then a No. 100 round sieve (150 μm) to obtain 132 kg of film-undercoated microgranules.
[Undercoating Film Solution]

| | |
|---|---|
| Hypromellose (type 2910, viscosity: 3 centistokes) | 9.24 kg |
| Titanium dioxide (TiO$_2$) | 3.96 kg |
| Sterilized talc (manufactured by Matsumura sangyo) | 3.96 kg |
| Low-substituted hydroxypropyl cellulose LH-32 (hydroxypropoxyl group content: 8.8% by weight) | 6.6 kg |
| Mannitol | 9.24 kg |
| Purified water | 99.0 L |

(3) Production of Enteric Coated Microgranules

The film-undercoated microgranules (44.0 kg) obtained in the above (2) was put into a rotating fluidized bed granulator (manufactured by Powlex, Model MP-400) and coated by spraying the predetermined amount 54.6 kg of an enteric film solution (A) of composition as described below, which was previously prepared, in a tangential spraying manner at a supply rate of 1.05 kg/min while the ventilation temperature was controlled so that the exhaust air temperature can be about 42° C. under steady state condition.
[Enteric Film Solution (A)]

| | |
|---|---|
| Eudragit L30D-55 | 32.05 kg |
| Eudragit NE30D | 3.570 kg |
| Polyethylene glycol 6000 | 1.071 kg |
| Glyceryl Monostearate | 0.629 kg |
| Polysorbate 80 | 0.189 kg |
| Ferric oxide | 0.006 kg |
| Yellow ferric oxide | 0.006 kg |
| Anhydrous citric acid | 0.013 kg |
| Purified water | 44.3 L |

Subsequently, the predetermined amount 201.6 kg of an enteric film solution (B) of composition as described below, which was previously prepared, was sprayed in a tangential spraying manner at a supply rate of 1.00 kg/min while the ventilation temperature was controlled so that the exhaust air temperature can be about 42° C. under steady state condition.
[Enteric Film Solution (B)]

| | |
|---|---|
| Eudragit L30D-55 | 117.6 kg |
| Eudragit NE30D | 13.06 kg |
| Triethyl citrate | 7.854 kg |
| Glyceryl Monostearate | 2.521 kg |
| Polysorbate 80 | 0.756 kg |
| Ferric oxide | 0.025 kg |
| Yellow ferric oxide | 0.025 kg |
| Anhydrous citric acid | 0.021 kg |
| Purified water | 59.7 L |

Subsequently, the predetermined amount 27.3 kg of an enteric film solution (A) of composition as described below, which was previously prepared, was sprayed in a tangential spraying manner at a supply rate of 1.05 kg/min while the ventilation temperature was controlled so that the exhaust air temperature can be about 42° C. under steady state condition.

(4) Production of β-Mannitol-Overcoated Enteric Coated Microgranules

Subsequently to the above (3), the predetermined amount a film solution of composition as described below, which was previously prepared, was sprayed in a tangential spraying manner at a supply rate of 0.64 kg/min while the ventilation temperature was controlled so that the exhaust air temperature can be about 42° C. under steady state condition. When spraying of the predetermined amount 29.4 kg of the film solution was completed, spraying was stopped. The coated particles thus obtained were continued to be dried as they are until the exhaust air temperature reached 65° C. Then, the coated particles were sieved through a No. 35 round sieve (420 μm) and then a No. 60 round sieve (250 μm) to obtain 106 kg of overcoated enteric coated microgranules.

The average particle diameter of the resulting overcoated enteric coated microgranules was 340 μm.
[Film Solution]

| | |
|---|---|
| Mannitol | 4.2 kg |
| Purified water | 25.2 L |

(5) Production of Additive Granulated Powder

Ground δ-mannitol (84.68 kg), low-substituted, hydroxypropyl cellulose (LH-33) (12.48 kg), crystalline cellulose (12.48 kg), crospovidone (6.24 kg) and aspartame (1.248 kg) were put into a fluidized bed granulation dryer (manufactured by Freund, Model FLO-N-120), and fluidized at an air supply amount of 22 m$^3$/min while the air supply temperature was lowered stepwise from 95° C. to 70° C. Thereto a total amount of a solution of δ-mannitol (3.744 kg) and anhydrous citric acid (1.248 kg) in purified water (28.29 kg) was sprayed at a supply rate of 2000 g/min. After completion of spraying, drying was performed until the exhaust air temperature became 55° C. to obtain dried powder. The resulting dried granules were subjected to size adjustment with a Comil having a screen size of 1.575 mmΦ (manufactured by Quadro) to obtain additive granulated powder.

(6) Production of Mixed Powder

The overcoated enteric coated microgranules (108.0 kg) obtained in the above (4), the additive granulated powder (117.4 kg) obtained in the above (5) and a flavor (STRAWBERRY DURAROME, Nihon Firmenich K.K.) (0.18 kg) were put into a tumbler mixer (manufactured by Showa Kagaku Kikai Kosakusyo, Model TM-1000), and mixed at a rotation number of 10 min$^{-1}$ for 10 minutes. Thereto magnesium stearate (2.4 kg) was further added, and they were mixed at a rotation number of 5 min$^{-1}$ for 2 minutes to obtain mixed powder.

(7) Production of Orally Disintegrating Tablet

The mixed powder (20 kg) was compressed with a flat-faced punch having 12 mmΦ and beveled edges at a tableting pressure of about 22 kN/punch, about 30 kN/punch and about 39 kN/punch and at a die temperature of 47° C. using a rotary tableting machine (manufactured by Kikusui Seisakusho Ltd., Model LIBRA II) to obtain tablets with a weight of 570 mg per tablet.

(8) Effect of Warming-Tableting

The hardness of the resulting tablets is shown in Table 1. In Table 1, the hardness of tablets produced by using additive granulated powder produced using β-mannitol in place of δ-mannitol in the above (5) is also shown.

TABLE 1

Relationship between average hardness and tableting pressure

| | | Tablet produced using additive granulated powder containing δ-mannitol | Tablet produced using additive granulated powder containing β-mannitol in place of δ-mannitol |
|---|---|---|---|
| Tableting pressure | 22 kN | 25.9 N | 21.0 N |
| | 30 kN | 39.5 N | 30.5 N |
| | 39 kN | 49.3 N | 33.9 N |

As seen from Table 1, the use of δ-mannitol could enhance the hardness of tablets, as compared with tablets produced using β-mannitol and the same tableting pressure.

INDUSTRIAL APPLICABILITY

According to the production method of the present invention, an orally disintegrating solid preparation having a suitable strength (hardness) can be produced, and therefore the occurrence of damage in the preparation can be suppressed when the preparation is subjected to a stress in conveying, packaging with the use of an automatic dispenser, taking out from a PTP and so on.

An orally disintegrating solid preparation obtained by the production method of the present invention has excellent disintegrating property or excellent solubility, and therefore it can be used in treating and preventing various diseases as a preparation which can be easily ingested by elderly people and children without water.

The invention claimed is:

1. A method of producing an orally disintegrating solid preparation, which comprises producing β-mannitol-overcoated enteric coated powders having a core containing an active pharmaceutical ingredient, producing additive powders containing δ-mannitol granulated by a fluidized bed granulation method, mixing the β-mannitol-overcoated enteric coated powders with the additive powders to produce mixed powders, and then tableting the mixed powders.

2. The method according to claim 1, wherein the granulation by a fluidized bed granulation method comprises a step of contacting δ-mannitol with an aqueous solvent.

3. The method according to claim 1, wherein the additive powders containing δ-mannitol further contains (i) crystalline cellulose and/or (ii) low-substituted hydroxypropyl cellulose.

4. The method according to claim 1, wherein the granulation by a fluidized bed granulation method comprises a step of spraying a δ-mannitol solution and a drying step.

5. The method according to claim 4, wherein the solution is an aqueous solution.

6. The method according to claim 1, wherein dried granules of the additive are produced by a fluidized bed granulation method and the resulting dried granules are subjected to size adjustment.

7. The method according to claim 1, wherein the active pharmaceutical ingredient is an acid-labile physiologically active substance.

8. The method according to claim 1, wherein the active pharmaceutical ingredient is a proton pump inhibitor (PPI).

9. The method according to claim 7, wherein the acid-labile physiologically active substance is a benzimidazole compound or a salt thereof.

10. The method according to claim 9, wherein the benzimidazole compound is lansoprazole or a salt thereof, or an optically active form thereof.

11. The method according to claim 1, wherein the average particle diameter of the β-mannitol-overcoated enteric coated powders is 400 μm or less.

12. The method according to claim 11, wherein a basic inorganic salt is present in the β-mannitol-overcoated enteric coated powders.

* * * * *